United States Patent [19]

Pedersen et al.

[11] Patent Number: 5,472,865
[45] Date of Patent: Dec. 5, 1995

[54] **PROTEASE FROM *DENDRYPHIELLA ARENARIA* DSM 6260 OR *DENDRYPHIELLA SALINA* DSM 6332, PROCESS FOR MAKING IT AND USE AS DETERGENT ADDITIVE**

[75] Inventors: Kim B. Pedersen, Copenhagen; Margrethe Christiansen, Klampenborg; Poul Lindegaard, Copenhagen, all of Denmark

[73] Assignee: Novo Nordisk A/S, Bagsvaerd, Denmark

[21] Appl. No.: 122,578

[22] PCT Filed: Apr. 10, 1992

[86] PCT No.: PCT/DK92/00117

§ 371 Date: Sep. 28, 1993

§ 102(e) Date: Sep. 28, 1993

[87] PCT Pub. No.: WO92/18622

PCT Pub. Date: Oct. 29, 1992

[30] Foreign Application Priority Data

Apr. 12, 1991 [DK] Denmark .................... 658/91

[51] Int. Cl.⁶ .................. C12N 9/58; C12N 1/14; C12N 9/96; C11D 17/00
[52] U.S. Cl. ............ 435/223; 252/174.12; 252/DIG. 12; 435/188; 435/254.1; 435/911
[58] Field of Search ............... 435/219, 223, 435/254.1, 911, 188; 252/DIG. 12, 174.12

[56] References Cited

FOREIGN PATENT DOCUMENTS

| 0224246 | 6/1987 | European Pat. Off. . |
| 0314401 | 5/1989 | European Pat. Off. . |
| 0335023 | 10/1989 | European Pat. Off. . |
| WO88/03948 | 6/1988 | WIPO . |

OTHER PUBLICATIONS

MacDonald et al., Can. J. Bot., vol. 60, 1982, pp. 838–844.
Michaelis et al., Mycolgia, 79(4), 1987, pp. 514–518.

*Primary Examiner*—David M. Naff
*Assistant Examiner*—Mike Meller
*Attorney, Agent, or Firm*—Steve T. Zelson; Karen A. Lowney

[57] ABSTRACT

A protease obtainable from *Dendryphiella arenaria* DSM 6260 or *Dendryphiella salina* DSM 6332 is disclosed. The protease has a pI of approximately 9.1 as determined by isoelectric focusing, a molecular weight of approximately 18–20 kD as determined by SDS-PAGE, is active towards haemoglobin, casein, skimmed milk, and Suc-Ala-Ala-Pro-Phe-pNA and has immunochemical properties identical to those of a protease obtained from *Dendryphiella arenaria* DSM 6260 or *Dendryphiella salina* DSM 6332. A process for its production, use in a detergent composition and as a detergent additive are disclosed.

9 Claims, No Drawings

PROTEASE FROM *DENDRYPHIELLA ARENARIA* DSM 6260 OR *DENDRYPHIELLA SALINA* DSM 6332, PROCESS FOR MAKING IT AND USE AS DETERGENT ADDITIVE

TECHNICAL FIELD

This invention is in the field of detergent proteases. More specifically, the invention is directed towards novel alkaline proteases derived from strains of imperfect fungi of the genus/genera Dendryphiella and/or Scolecobasidium. Moreover, the invention is directed towards a process for preparation of the proteases, the use of the proteases as detergent enzyme, and detergent compositions comprising the proteases of the invention.

BACKGROUND ART

Detergent enzymes have been marketed for more than 20 years and are now well established as normal detergent ingredients in both powder and liquid detergents all over the world. With the trend towards lower temperature washing, detergent enzyme consumption has increased during late years. Enzymes used in washing formulations comprise proteases, lipases, amylases, cellulases, as well as other enzymes, or mixtures hereof. Commercially most important are proteases.

Detergent proteases have been developed by isolation of proteases found in nature followed by testing in detergent formulations. Most detergent proteases are obtained from members of the genus Bacillus. Currently new types of proteases enter the market, offering the possibility of giving a better cost/performance ratio at various specified conditions.

Examples of commercial protease products are ALCALASE™, ESPERASE™ and SAVINASE™, all supplied by Novo Nordisk AS, Denmark. These and similar enzyme products from other commercial sources are active in detergent solutions, i.e. at pH values in the range of from 8 to 11 and in the presence of sequestering agents, surfactants and bleaching agents, such as sodium perborate. The ALCALASE™ protease is produced by strains of the species *Bacillus licheniformis*. The ESPERASE™ and SAVINASE™ proteases are obtained by cultivation of strains of alkalophilic bacilli.

SUMMARY OF THE INVENTION

According to the present invention novel detergent proteases are provided. In its first aspect, the invention provides a protease obtainable from a strain of the genus Dendryphiella or Scolecobasidium.

In a more specific aspect, the invention provides a protease having a pI of approximately 9.1, a molecular weight of approximately 18–20 kD, being active towards haemoglobin, casein, skimmed milk and Suc-Ala-Ala-Pro-Phe-pNA, and having immunochemical properties identical or partially identical to those of a protease derived from the strain *D. arenaria*, DSM No. 6260, or the strain *D. salina*, DSM No. 6331.

In another specific aspect, the invention provides a protease having a pI>9.5, a molecular weight of approximately 28 kD, and immunochemical properties identical or partially identical to those of a protease derived from *Dendryphiella arenaria*, DSM No. 6260.

In its second aspect, the invention provides a process for the preparation of the proteases comprising cultivation of a protease producing strain of the genus Dendryphiella or Scolecobasidium in a suitable nutrient medium, containing carbon and nitrogen sources and inorganic salts, followed by recovery of the desired enzyme.

In its third aspect, the invention provides a process for the preparation of the protease which process comprises isolating a DNA fragment encoding the protease, combining the DNA fragment with an appropriate expression signal in an appropriate plasmid vector, introducing the plasmid vector into an appropriate host either as an autonomously replicating plasmid or integrated into the chromosome, cultivating the host organism under conditions leading to expression of the protease, and recovering of the protease from the culture medium.

In its fourth aspect, the invention claims the use of the proteases as detergent enzymes. In a more specific embodiment of this aspect, the invention provides detergent compositions comprising the proteases. In another specific embodiment of this aspect, the detergent compositions are provided in the form of a detergent additive, preferably a non-dusting granulate or a stabilized liquid.

DETAILED DISCLOSURE OF THE INVENTION

The Organism

The new detergent proteases of the invention can be provided from members of the genera Dendryphiella and Scolecobasidium. Dendryphiella and Scolecobasidium belong to the Fungi Imperfecti. *D. salina* (Sutherland) Pugh et Nicot (synonyms: *S. salinum* (Sutherland) M. B. Ellis, *Cercospora salina* (Sutherland) and *D. arenaria* Nicot (synonyms: *S. arenarium* (Nicot) M. B. Ellis) are two closely related species that are commonly isolated from marine habitats in near-shore areas. Examples are the strains *D. arenaria* Nicot, DSM 6260 that was originally isolated from a decomposing *Nereocystis alga,* and *D. salina* (Sutherland) Pugh et Nicot, DSM 6331. Other species are e.g.:

*D. vinosa* (Bert. & Curt) Reisinger;

*D. infuscans* (Thümen) M. B. Ellis;

*S. cateniphorum* Matsushima;

*S. echinophilum* (Massalongo) Sutton;

*S. fusiforme* Matsushima;

*S. longiphorum* Matsushima;

*S. salmonicolor* Shearer;

*S. terreum* Abbot;

*S. tshawytschae* (Doty & Slater) McGinnis & Ajello;

*S. constrictum* Abbot;

*S. humicola* Barron & Busch;

*S. obovatum* Matsushima;

*S. variabile* Barron & Busch;

*S. anelli* Graniti;

*S. verruculosum* Roy, Dwivedi & Mishra;

*S. gyrocarpi* M. B. Ellis;

An example is a strain of *S. gyrocarpi* M. B. Ellis, DSM 6332.

Cultivation of the Microorganism

The microorganisms can be cultivated under aerobic conditions in nutrient media containing assimilable carbon and nitrogen sources together with other essential nutrients, the media being composed in accordance with the principles of the known art. Strains of *D. salina* and *D. arenaria* can be cultivated in media based on sea water or containing sea salts, but it is not a prerequisite.

The organisms are e.g. able to grow at room temperature on many commonly used agar media like PDA (Potato Dextrose Agar), YPG (4 g/l yeast extract; 15 g/l glucose; 1 g/l $K_2HPO_4$; 0.5 g/l $MgSO_4$,7 $H_2O$; 20 g/l agar; pH 7.3–7.5 is before sterilization) and Bacto Yeast Morphology Agar (Difco™). *D. arenaria* and *D. salina* are also able to grow on KMV agar (1 g/l glucose; 0.1 g/l yeast extract; 0.1 g/l Bacto™ peptone; 1 g/l gelatin hydrolysate; 12 g/l agar; 40 g/l Sigma™ Sea Salts).

Suitable carbon sources are carbohydrates such as sucrose, glucose and starch, or carbohydrate containing materials such as soy bean grits, cotton seed flour, cereal grain, malt, rice and sorghum. The carbohydrate concentration incorporated in the medium may vary widely, e.g. up to 25% and down to 0.1%, but usually 1%–10% will be suitable.

The nitrogen source in the nutrient medium may be of inorganic and/or organic nature. Suitable inorganic nitrogen sources are nitrates and ammonium salts. Among the organic nitrogen sources quite a number are regularly used in fermentation processes. Illustrative examples are soybean meal, cotton seed meal, peanut meal, casein, corn, corn steep liquor, yeast extract, urea and albumin. In addition, the nutrient medium should also contain usual trace substances.

Recovery and Purification of the Proteases

After fermentation, the extracellular proteases produced by the fungi can be recovered and purified according to principles of the known art, e.g. using steps like removal of coarse materials from the culture broth by centrifugation or drum filtration, concentration of the broth by evaporation or ultrafiltration, and purification by anion-exchange chromatography. Finally, preservatives may be added to the purified proteases.

Recombinantly Produced Proteases

The proteases of the invention can also be obtained by recombinant DNA-technology.

A process for the preparation of the protease may comprise isolating a DNA fragment encoding the protease, combining the DNA fragment with an appropriate expression signal in an appropriate plasmid vector, introducing the plasmid vector into an appropriate host either as an autonomously replicating is plasmid or integrated into the chromosome, cultivating the host organism under conditions leading to expression of the protease, and recovering the protease from the culture medium. The various steps that constitute this recombinantly process are methods known in the art per se.

Preferred host organisms are *E. coli*, or members of the genus Bacillus, Aspergillus, or Streptomyces.

Assay for Proteolytic Activity

The proteolytic activity is determined with casein as substrate. One Casein Protease Unit (CPU) is defined as the amount of enzyme liberating 1 mM of primary amino groups (determined by comparison with a serine standard) per minute under standard conditions, i.e. incubation for 30 minutes at 25° C. and pH 9.5. A folder AF 228, describing the analytical method, is available upon request to Novo Nordisk A/S, Denmark, which folder is hereby included by reference.

The Enzyme

The enzymes of the invention are novel detergent proteases. The enzymes are obtainable from strains of the genera Dendryphiella and Scolecobasidium, e.g. from strains of *D. salina, D. arenaria*, or *S. gyrocarpi*, e.g. the strain *D. arenaria*, DSM 6260, *D. salina*, DSM 6331, or *S. gyrocarpi*, DSM 6332.

The proteases of the invention are alkaline proteases with isoelectric points (pI) as determined by LKB PAG plates (pH 3.5–9.5) above 8.0.

A particular protease of the invention is a protease having a pI of approximately 9.1, a molecular weight of approximately 18–20 kD, being active towards haemoglobin, casein, skimmed milk and Suc-Ala-Ala-Pro-Phe-pNA, having immunochemical properties identical or partially identical to those of a protease derived from the strain *D. arenaria*, DSM No. 6260, or the strain *D. salina*, DSM No. 6331.

Another particular protease of the invention is a protease having a pI 9.5, a molecular weight of approximately 28 kD, and immunochemical properties identical or partially identical to those of a protease derived from *Dendryphiella arenaria*, DSM No. 6260.

Immunochemical Properties

The immunochemical properties can be determinated immunologically by cross-reaction identity tests. The identity tests can be performed by the well-known Ouchterlony double immunodiffusion procedure or by tandem crossed immunoelectrophoresis according to N. H. Axelsen; Handbook of Immuno-precipitation-in-Gel Techniques; Blackwell Scientific Publications (1983), chapters 5 and 14. The terms "antigenic identity" and "partial antigenic identity" are described in the same book, chapters 5, 19 and 20.

Detergent Compositions

The detergent composition of the invention may comprise one or more surfactants which may be of an anionic, non-ionic, cat-ionic, amphoteric or zwitter-ionic type, or a mixture of these. Typical examples of anionic surfactants are linear alkyl benzene sulfonates (LAS), alkyl sulfates (AS), alpha olefin sulfonates (AOS), alcohol ethoxy sulfates (AES) and alkali metal salts of natural fatty acids. Examples of non-ionic surfactants are alkyl polyethylene glycol ethers, nonylphenol polyethylene glycol ethers, fatty acids esters of sucrose and glucose, and esters of polyethoxylated alkyl glucoside.

The detergent composition of the invention may also contain other detergent ingredients known in the art such as builders, bleaching agents, bleach activators, anti-corrosion agents, sequestering agents, anti soil-redeposition agents, perfumes, stabilizers for the enzymes and bleaching agents, formulations aids, optical brighteners, foam boosters, chelating agents, fillers, fabric softeners, etc. The detergent composition of the invention may be formulated substantially as described in J. Falbe [Falbe, J.; Surfactants in Consumer Products. Theory, Technology and Application; Springer Verlag 1987, vide in particular the section entitled "Frame formulations for liquid/powder heavy-duty detergents"].

It is at present contemplated that the detergent composition of the invention may contain the enzyme preparation in an amount corresponding to 0.0005–0.5 CPU of the proteolytic enzyme per liter of washing liquor.

The detergent compositions of the invention can be formulated in any convenient form such as powders, liquids, etc.

The detergent composition of the invention may advantageously include one or more other enzymes, e.g. lipases, amylases, cellulases, oxidases and/or peroxidases, conventionally included in detergent compositions.

The protease of the invention may be included in a detergent composition by adding separate additives containing the detergent protease, or by adding a combined additive comprising different detergent enzymes.

The additive of the invention can be formulated e.g. as granulates, liquids, slurries, etc. Preferred detergent additive formulations are non-dusting granulates or stabilized liquids. Dust free granulates may be produced e.g. according to GB Patent Publication No. 1,362,365 or U.S. Pat. No.

4,106,991, and may optionally be coated by methods known in the art. The detergent enzymes may be mixed before or after granulation. Liquid enzyme preparations may, for instance, be stabilized by adding a polyol such as e.g. propylene glycol, a sugar or sugar alcohol, lactic acid or boric acid, according to established methods. Other enzyme stabilizers are well known in the art. Protected enzymes may be prepared according to the method disclosed in EP Patent Publication No. 238,216.

The invention is further illustrated in the following examples, which are not intended to be in any way limiting to the scope of the invention as claimed.

EXAMPLE 1

Cultivation Example

The strain *D. arenaria*, DSM No. 6260, was cultivated at 18° C. for 7 days on a rotary shaking Table (250 r.p.m.) in 100 500 ml baffled Edenmeyer flasks containing 100 ml of medium of the following composition (per liter):

| | |
|---|---|
| Soy grits | 50 g |
| $MgSO_4;7H_2O$ | 0.2 g |
| $Na_2HPO_4;2H_2O$ | 10 g |
| $K_2HPO_4$ | 2 g |
| Glucose | 10 g |
| Pluronic ® L-61 | 0.1 ml |
| pH adjusted to 7.0 before autoclaving. | |

After cultivation, the enzyme activity of the broth was 3.7 CPU/l.

The strain *D. salina*, DSM No. 6331, was cultivated in a similar way with the exception that the cultivation medium further contained 40 g/l Sigma Sea Salts.

After cultivation, the enzyme activity of the broth was 5.2 CPU/l. The broth contained one major protease component with a pI of approximately 9.1.

EXAMPLE 2

Purification Example

The culture broth of *D. arenaria*, DSM 6260, as obtained according to Example 1, was centrifuged in a Beckman J-6 centrifuge at 4000 rpm for 30 minutes. The supernatant was collected and filtered through a 10/µm filter net.

Thus, 7.5 liters of supernatant were obtained that were subsequently concentrated into 1.0 kg by ultrafiltration with a 1000 cut-off polysulphon membrane using a Filtron equipment.

The proteases were further purified by anion-exchange chromatography followed by affinity chromatography on a HPLC column.

For the anion-exchange the concentrate obtained above was reacted in a batch process with DEAE-Sephadex A-50 in 25 mM borate, 5 mM $CaCl_2$; pH 8.5. The proteases remain in the material not binding to the matrix.

The affinity chromatography of the protease-containing material from the anion-exchange was carried out on a HPLC column.

The protease preparation thus obtained contained two proteases. The major component of the protease preparation obtained by cultivation of the strain *D. arenaria*, DSM No. 6260, was characterized by a pI of 9.1 as determined by isoelectric focusing on LKB Ampholine® PAG plates (pH 3.5–9.5) and a MW of approximately 20,000 as determined by SDS-PAGE. The minor component was characterized by a pI of >9.5 and a MW of approximately 28,000. As judged by SDS-PAGE, the proteases comprised approximately 50% of the total protein content.

The major protease component is further characterized by its ability to cleave casein (Hammarsten®), haemoglobin, skimmed milk, and N-succinyl-Ala-Ala-Pro-Phe-p-nitroanilide. The protease has none or very low activity towards the chromogenic substrates BAPNA (N-α-benzoyl-$_{DL}$-Arg-p-nitroanilide) and Z-Glu-pNA (N-benzyloxycarbonyl-Glu-p-nitroanilide). The protease is not inhibited by EDTA.

Proteases obtained by cultivation of the strain *D. salina*, DSM No. 6331 was purified essentially as described above. It was further characterized by a MW of approximately 18,000–20,000 as determined by SDS-PAGE, by its ability to cleave casein (Hammarsten®), haemoglobin, skimmed milk, and N-succinyl-Ala-Ala-Pro-Phe-p-nitroanilide. The protease has none or very low activity towards the chromogenic substrates BAPNA and Z-Glu-pNA.

EXAMPLE 3

Wash Performance

The wash performance tests were accomplished in a model wash on grass juice soiled cotton at 20° C., isothermically for 10 minutes.

Two American Type detergent formulations were used in the test, a powder detergent composition and a liquid detergent composition. The enzyme preparations described in Example 2 were used for the washing tests. The enzyme dosage used is cited in the tables below. The textile/wash liquor ratio was 6 g of textile per liter of wash liquor.

2.0 g/l of a commercial American Type powder detergent were used. The detergent was dissolved in approx. 6° dH (German Hardness) water. The pH was 9.5.

2.0 g/l of a commercial American Type liquid detergent were used. The detergent was dissolved in approx. 6° dH water. The pH was 7.8.

Subsequent to washing, the fabric was rinsed in running tap water for 25 minutes and air-dried. The protease performance was determined by the change (ΔR) of the remission (%R) at 460 nm measured on a Datacolor Elrephometer 2000, ΔR being the remission after wash with protease added minus the remission after wash with no protease added.

The results of the test are shown in Tables 1 and 2.

TABLE 1

The differential remission, Δ R, measured after wash in an American Type powder detergent composition.

| | Enzyme dosage (CPU/l) | | | | | |
|---|---|---|---|---|---|---|
| | 0.0025 | 0.005 | 0.01 | 0.05 | 0.1 | 0.2 |
| *D. arenaria* protease | 4.0 | 6.6 | 11.7 | 20.2 | 21.6 | 21.6 |
| *D. salina* protease | 6.5 | 14.3 | 20.6 | 23.4 | 24.2 | — |

TABLE 2

The differential remission, Δ R, measured after wash in an American Type liquid detergent composition.

| | Enzyme dosage (CPU/l) | | | | | |
|---|---|---|---|---|---|---|
| | 0.01 | 0.04 | 0.08 | 0.16 | 0.50 | 1.0 |
| *D. arenaria* protease | 7.1 | 13.4 | 16.5 | 18.2 | — | — |

TABLE 2-continued

The differential remission, Δ R, measured after wash in an American Type liquid detergent composition.

| | Enzyme dosage (CPU/l) | | | | | |
|---|---|---|---|---|---|---|
| | 0.01 | 0.04 | 0.08 | 0.16 | 0.50 | 1.0 |
| D. salina protease | 5.2 | 12.5 | 15.8 | 17.9 | 19.5 | 20.3 |

As indicated by the differential remission values, the proteases of the invention are suitable for use as detergent enzymes.

EXAMPLE 4

Isolation of Separate Protease Components

The strain D. arenaria, DSM No. 6260, was cultivated in a Chemap fermentor for 160 hours in 10 l of the following substrate:

| | |
|---|---|
| Soy flakes | 50 g/l |
| MgSO$_4$;7H$_2$O | 0.2 g/l |
| Na$_2$HPO$_4$;2H$_2$O | 10 g/l |
| K$_2$HPO$_4$ | 2 g/l |
| Glucose | 10 g/l |
| Pluronic ® L61 | 1 ml/l |
| pH adjusted to 7.0 before sterilisation | |

During the fermentation, the pH was kept below 8.0 by addition of dilute H$_3$PO$_4$.

The culture broth was concentrated as described in Example 2.

The pH of the concentrate was adjusted to 7.5. To 100 ml of this were added 70 ml of acetone, and the precipitate was removed by centrifugation and discarded. To the supernatant were added 100 ml of acetone. The precipitate containing the proteases was recovered by centrifugation and dissolved in 25 mM borate, 5 mM CaCl$_2$; pH 8.5.

This material was purified by anion-exchange and affinity chromatography as described in Example 2.

The two proteases in the eluate from the HPLC affinity chromatography were separated by cationic-exchange chromatography on a Mono S HR 5/5 column (Pharmacia). The eluate from the HPLC column was dialyzed overnight against a buffer containing 20 mM Na-acetate, 50 mM boric acid, 2 mM CaCl$_2$; pH 4.5. This was applied to a Mono S column, from which the two proteases in a gradient of NaCl were eluted in separate fractions.

As judged by SDS-PAGE, the purity of the major protease component with pI 9.1 and MW 20,000 was more than 90%.

The preparation of the minor protease component with pI>9.5 and MW 28,000 was more than 50% pure, but still contained a significant amount of another protein with MW as judged by SDS-PAGE of approximately 33,000. The contaminating protein contained no proteolytic activity.

EXAMPLE 7

N-terminal Sequences

The major components of the protease preparations obtained as described above were subjected to N-terminal sequence determination.

The N-terminal sequence of the major component from the strain D. arenaria, DSM No. 6260, was found to be:

A-T-V-R-G-G-D-A-Y-Y-I-N-R-A-G-R-S-S-V-G-F-S(SEQ ID NO:1)

The N-terminal sequence of the major component from the strain D. salina, DSM No. 6331, was found to be:

X-X-V-R-G-G-D-A-Y-Y-I-N-R-A-G-R-X-S-V-G-F-S-V-S-G-G-Y-V-S-A- (SEQ ID NO:2)

The N-terminal sequences of the Dendryphiella proteases are virtually identical, and the proteases, therefore, are closely related.

We claim:

1. A protease, obtainable from a microorganism strain selected from the group consisting of *Dendryphiella arenaria* DSM 6260 and *Dendryphiella salina* DSM 6332 having the following properties:

(a) a pI of approximately 9.1 as determined by isoelectric focusing;
   (b) a molecular weight of approximately 18–20 kD as determined by SDS-PAGE;
   (c) being active towards haemoglobin, casein, skimmed milk, and Suc-Ala-Ala-Pro-Phe-pNA; and
   (d) immunochemical properties identical to those of a protease obtained from said strain.

2. A protease, obtainable from *Dendryphiella arenaria* DSM-6260 having the following properties:

(a) a pI>9.5 as determined by isoelectric focusing;
   (b) a molecular weight of approximately 28 kD as determined by SDS-PAGE; and
   (c) immunochemical properties identical to those of a protease derived from said *Dendryphiella arenaria*, DSM No. 6260.

3. A process for the preparation of a protease according to claim 1 or 2, which process comprises cultivation of a strain which produces said protease in a suitable nutrient medium, containing carbon and nitrogen sources and inorganic salts, followed by recovery of said protease.

4. A detergent composition comprising a protease according to claim 1 or 2 and a surfactant.

5. The detergent composition according to claim 4, which further comprises one or more enzymes selected from the group consisting of amylases, lipases, cellulases, oxidases and peroxidases.

6. A detergent additive comprising said protease according to claim 1 or 2, in the form of a non-dusting granulate or a liquid.

7. A detergent additive comprising said protease according to claim 1 or 2 in the form of a stabilized liquid.

8. A detergent additive comprising said protease according to claim 1 or 2 in the form of a slurry.

9. A detergent additive comprising said protease according to claim 1 or 2 in the form of a protected enzyme.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 28 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:1:

```
Ala  Thr  Val  Arg  Gly  Gly  Asp  Ala  Tyr  Tyr  Ile  Asn  Arg  Ala  Gly  Arg
 1                   5                                 10                                15

Ser  Ser  Val  Gly  Phe  Ser  Val  Ser  Xaa  Gly  Tyr  Val
                     20                        25
```

( 2 ) INFORMATION FOR SEQ ID NO:2:

( i ) SEQUENCE CHARACTERISTICS:
      ( A ) LENGTH: 30 amino acids
      ( B ) TYPE: amino acid -continued (D) TOPOLOGY: linear (ii) MOLECULE TYPE: peptide (xi) SEQUENCE DESCRIPTION: SEQ ID NO:2:

| Xaa | Xaa | Val | Arg | Gly | Gly | Asp | Ala | Tyr | Tyr | Ile | Asn | Arg | Ala | Gly | Arg |
| 1 | | | | 5 | | | | | 10 | | | | | 15 | |
| Xaa | Ser | Val | Gly | Phe | Ser | Val | Ser | Gly | Gly | Tyr | Val | Ser | Ala | | |
| | | | 20 | | | | | 25 | | | | | 30 | | |